United States Patent [19]

Marnay et al.

[11] Patent Number: 5,713,899
[45] Date of Patent: Feb. 3, 1998

[54] CERVICAL CAGE DESIGNED FOR THE PERFORMANCE OF INTERSOMATIC ARTHRODESIS

[75] Inventors: Thierry Marnay, Nimes; Jean Huppert, L'Etrat; Salvatore Sessa, Paris; Joël Godard, Besancon, all of France

[73] Assignee: Societe JBS SA, Sainte-Savine, France

[21] Appl. No.: 638,383

[22] Filed: Apr. 26, 1996

[30] Foreign Application Priority Data

Apr. 27, 1995 [FR] France ..................... 95 05244

[51] Int. Cl.⁶ ..................................... A61B 17/70
[52] U.S. Cl. ............................. 606/61; 623/17
[58] Field of Search ..................... 606/60, 61, 78; 623/17

[56] References Cited

U.S. PATENT DOCUMENTS

| | | |
|---|---|---|
| 5,192,327 | 3/1993 | Brantigan ................. 623/17 |
| 5,246,443 | 9/1993 | Mai ......................... 606/78 |
| 5,554,191 | 9/1996 | Lahille et al. ............. 623/17 |

FOREIGN PATENT DOCUMENTS

| | | |
|---|---|---|
| 0179695 | 4/1986 | European Pat. Off. . |
| 0307241 | 3/1989 | European Pat. Off. . |
| 9405235 | 3/1994 | European Pat. Off. . |
| 2703580 | 3/1993 | France . |
| 1107854 | 3/1983 | U.S.S.R. . |
| 1818091 | 5/1993 | U.S.S.R. . |
| 9405235 | 9/1992 | WIPO . |
| 9501763 | 1/1995 | WIPO . |

Primary Examiner—Michael Buiz
Assistant Examiner—David O. Reip
Attorney, Agent, or Firm—Harrison & Egbert

[57] ABSTRACT

The present invention is a cervical cage device designed to perform an intersomatic arthrodesis. It is made from a flat and elongated metal plate (1) wider in its central part (2), whose edges, except in the central part, have teeth (30, 40). The plate (1) is bent to form an open ring and the teeth (30, 40) are oriented toward the central part of the cage, so that the ends of the ring have the shape of spears.

5 Claims, 4 Drawing Sheets

1

CERVICAL CAGE DESIGNED FOR THE PERFORMANCE OF INTERSOMATIC ARTHRODESIS

TECHNICAL FIELD

This invention concerns a cervical cage device which permits the performance of an intersomatic arthrodosis.

BACKGROUND ART

Whenever a lesion of an intervertebral disk occurs, it is necessary to perform the removal thereof, and so as to correct its absence, it is necessary to perform an intersomatic arthrodesis, i.e., to fuse the vertebral body of both adjacent vertebrae to the disk while filling the void created by the removal.

Among the techniques used to date, the most common consist of using either a plate made integral with both vertebral bodies through outside screws, or a porous polyethylene intervertebral plate placed between both vertebral bodies. In both cases, a bone substitute or graft is inserted between both vertebral bodies to achieve their fusion.

However, the devices used present some disadvantages among which the main disadvantage is the use of screws which might loosen.

This disadvantage is common to all protheses, but it can have especially serious consequences when it concerns the sensitive area of the spine.

In addition, the use of polyethylene can have pathological consequences because of the particles which may break off from the plate.

Furthermore, the technique consisting of using an intervertebral plate requires the availability during surgery of a large number of plates of various sizes and thicknesses.

SUMMARY OF THE INVENTION

The purpose of this invention is a cervical cage designed to perform an intersomatic arthrodesis which eliminates all those various disadvantages.

The cervical cage device under this invention mainly characterized by the fact that it is made from a preferably titanium-based, flat and elongated metal plate, wider in its central part and whose edges, except in the central pasta have a serrated profile, and that the plate is bent to form an open ring.

According to a further characteristic of the device under the invention, the teeth on the extreme edges are oriented toward the central part of the cage, so that both ends of the ring have the shape of spears.

According to a further characteristic of the device under the invention, the central part of the cage has a tapped hole which allows for the interlocking of a setting tool.

In a special embodiment of the device under the invention, the device features on each side of the central part and perpendicular thereto, two sharp and jagged points, folded at right angles on the side of the cage bend.

In another embodiment of the device under invention, the device features on each side of the central part and perpendicular thereto, two mounting lugs at the end of which a hole has been made to let a self-retaining screw through.

The cervical cage device under the invention designed to be placed between the vertebral bodies of two vertebrae to be fused, with the teeth which advantageously come to rest on the cortex so as to prevent it from sliding while a bone graft placed inside is used to use the vertebral bodies.

The advantages and characteristics of this invention will become more evident in the description below related to the attached drawings which represents an non-limiting embodiment.

DETAILED DESCRIPTION OF THE INVENTION

Figure 1:
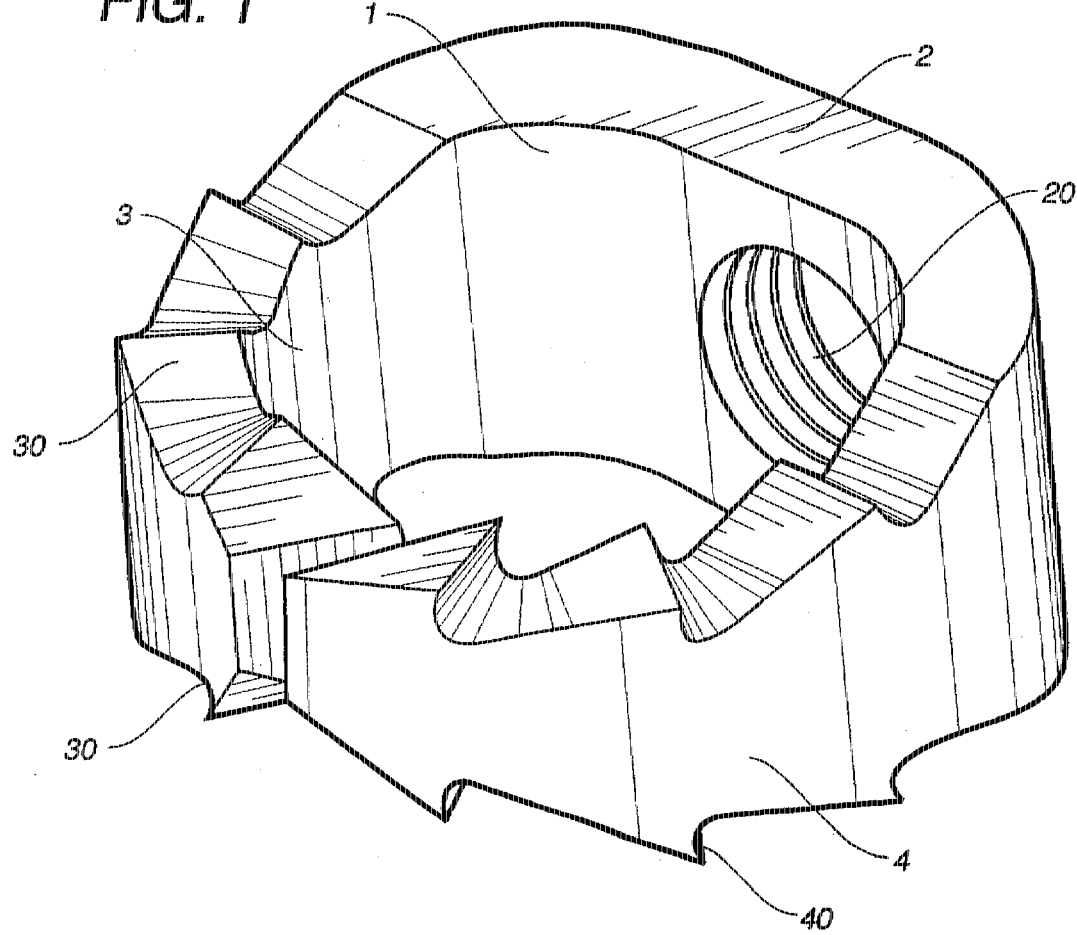
FIG. 1 represents a view in perspective of a first embodiment or the device under the invention.
Figure 2:
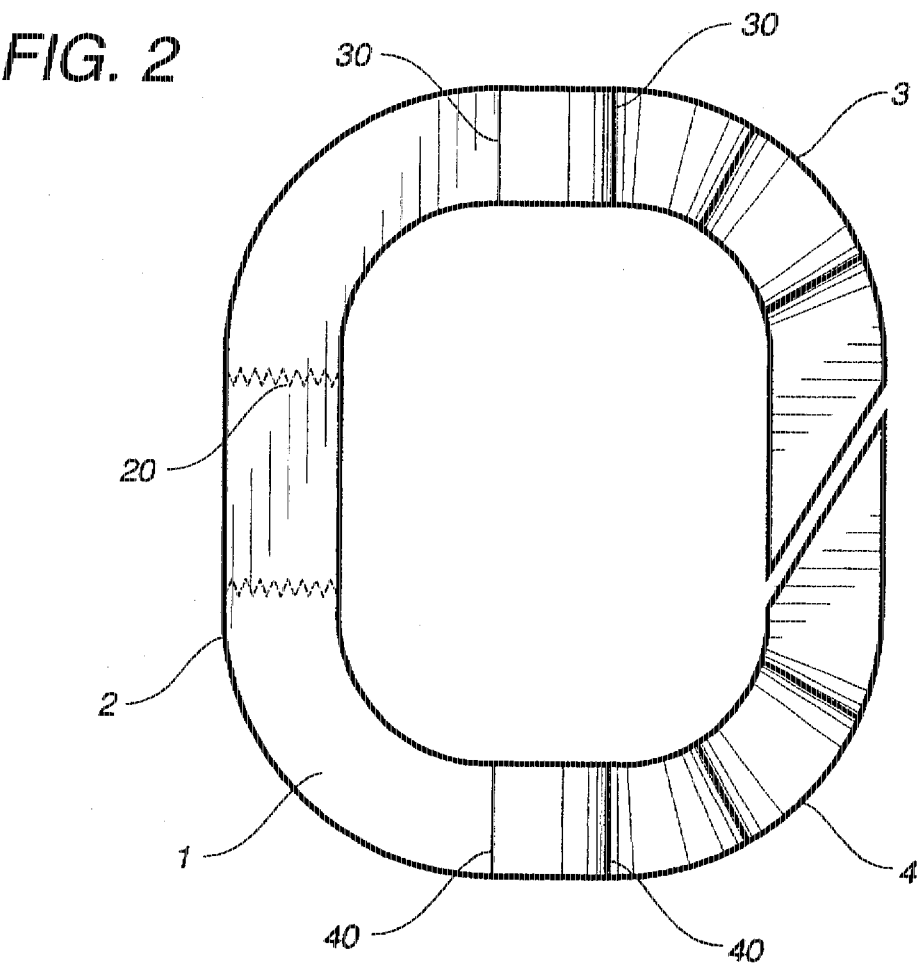
FIG. 2 represents a top view of the same device.
Figure 3:
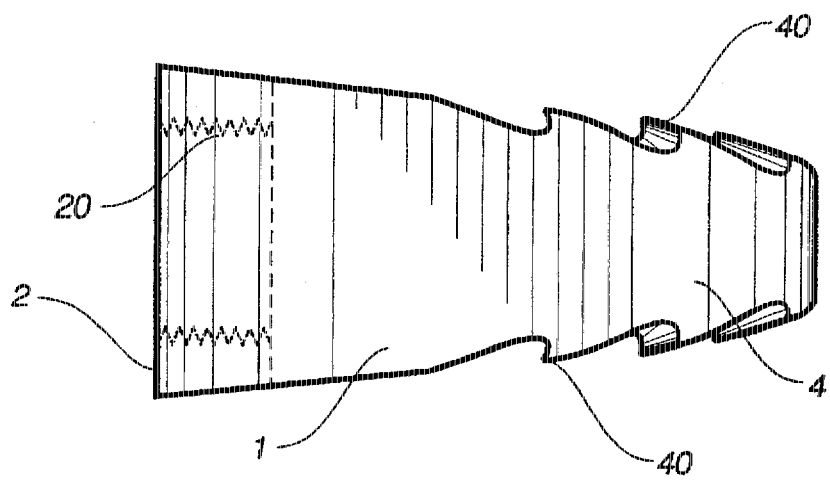
FIG. 3 represents a side view of the same device.

Referring to FIGS. 1, 2 and 3, it can be seen that a cervical cage device under the invention includes a flat and elongated plate 1 in which the central part 2 is wider than the narrowing extreme parts 3 and 4 and is bent so as to form an open flat ring.

The edges of the extreme parts 3 and 4 are serrated. The parts 3 and 4 have teeth 30 and 40 oriented toward the central part 2 so that the extreme parts 3 and 4 have the shape of spears.

The central part 2 has a tapped hole 20 to accommodate a setting tool (not shown) which is a rod with one threaded end.

The installation of a cervical cage under the invention is carried out as described hereinafter. After removal of the intervertebral disk and of the bordering cartilage plates, the vertebral bodies are moved apart and the cage containing a bone graft is inserted between the bodies. Beforehand, the extreme parts 3 and 4 of the cage, whose height will have been selected based on the intervertebral space to be filled, are moved apart more or less depending on the size of the vertebral bodies. After releasing the pressure applied on the vertebrae, teeth 30 and 40 bite into the cortex of the vertebral bodies. The spear shape of the teeth 30 and 40 prevents the cage from sliding. "The adjustable width" and ending "vary only in height" and insert therefor. The adjustable diameter of the cage is achieved by the ability to move extreme parts 3 and 4 toward each other or away from each other. This adjustability reduces the number of cage sizes required for surgery. The cages will only vary in its height dimension.

Figure 4:
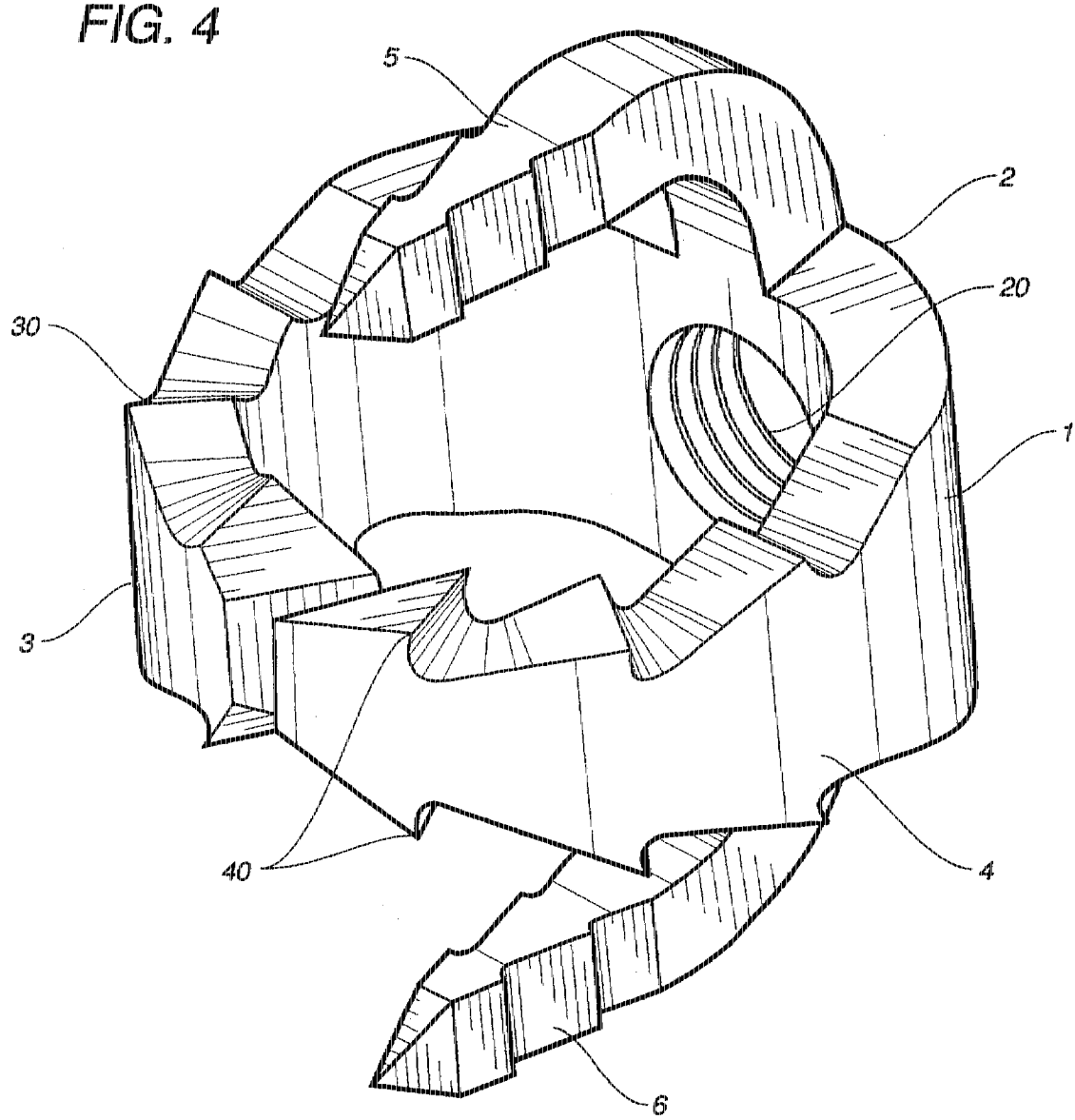
FIG. 4 represents a view in perspective of a second embodiment of the device under the invention.

Referring to FIG. 4, it can be seen in a second embodiment that the cervical cage device under the invention features on each side of central part 2, two sharp and jagged points 5 and 6, folded at right angles on the side of extreme parts 3 and 4.

Points 5 end 6 are designed to be forced into the vertebral bodies which will have been previously pierced with a template used to define the adequate gap between the vertebral bodies.

Points 5 end 6 complete the cage fixture and maintain the gap between said vertebral bodies.

It should be noted that those points can be made out of a shape-memory metal so that at body temperature a slight contraction occurs.

Figure 5:
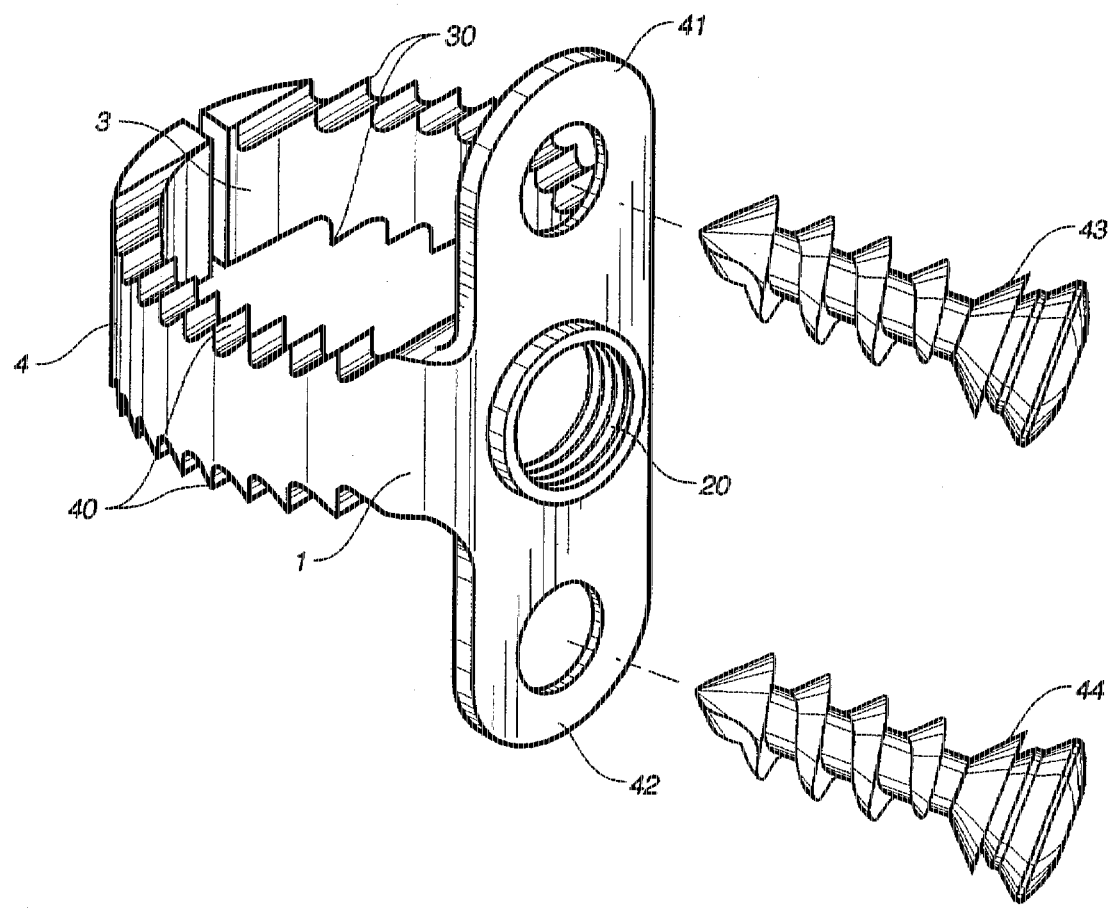
FIG. 5 is a perspective view of the mounting lugs as used in the present invention.

According to another embodiment shown in FIG. 5, the cage has, two mounting lugs 41 and 42 formed on each side of the central part. A hole has been made at the end of each of the mounting lugs 41 and 42 to let self-retaining screws 43 and 44, respectively.

It is obvious that this invention is not limited to the above description of a few embodiments which can be be subject to a number of modifications without being outside the scope of the invention.

We claim:

1. A cervical cage device for performing an intersomatic arthrodesis comprising:

a deformable open ring having a central part and two extreme parts, said extreme parts being adapted to be moved apart from or closer to one another such that said cage has a width which is adjustable to a size of two vertebral bodies between which the cage is to be inserted, each of said extreme parts having a first edge provided with teeth adapted to engage one of the vertebral bodies and a second edge with teeth adapted to engage the other vertebral body, said teeth of said extreme parts being oriented such that a narrow end of said teeth is directed toward said central part, each of said extreme parts having a spear-shaped configuration; and a mounting means secured to said central part of said open ring and extending perpendicularly thereto on both sides of said central part, said mounting means for fastening said open ring to the vertebral bodies and for maintaining a space between the vertebral bodies.

2. The cervical cage device of claim 1, wherein said central part has a tapped hole for receiving a setting tool therein.

3. The cervical cage device of claim 1, wherein said mounting means comprises a first sharp and toothed point folded at a right angle on one side of said open ring and a second sharp and toothed point folded at a right angle on an opposite side of said open ring, said first and second sharp and toothed points being adapted for being forced into the vertebral bodies.

4. The cervical cage device of claim 3, wherein said first and second sharp and toothed points are made of shape-memory metal.

5. The cervical cage device of claim 1, wherein said mounting means comprises a first mounting lug extending on one side of said open ring, and a second mounting lug extending on an opposite side of said open ring, each of said mounting lugs having an end with a hole formed therein, said hole for receiving a self-retaining screw adapted to be screwed into one of the two vertebral bodies.

* * * * *